United States Patent [19]

Bacchelli

[11] Patent Number: 4,616,654

[45] Date of Patent: Oct. 14, 1986

[54] FIELD PRODUCING INSTRUMENT FOR THE ELECTROTHERAPEUTIC SELF-TREATMENT OF PAIN AND INSOMNIA

[76] Inventor: Luciano Bacchelli, 4, rue d'Orzival, Sierre Vallese, Switzerland

[21] Appl. No.: 658,861

[22] Filed: Oct. 9, 1984

[30] Foreign Application Priority Data

Oct. 18, 1983 [IT] Italy ............................. 12019 A/83

[51] Int. Cl.⁴ ............................................... A61N 1/20
[52] U.S. Cl. ................................. 128/391; 128/419 R
[58] Field of Search ................................ 128/384–385, 128/387–392, 419 R, 907

[56] References Cited

U.S. PATENT DOCUMENTS

| | | | |
|---|---|---|---|
| 792,637 | 6/1905 | Wenigman | 128/387 |
| 867,721 | 10/1907 | Hatzenbuehler | 128/387 |
| 1,123,370 | 1/1915 | Pratt | 128/391 |
| 4,100,920 | 7/1978 | LeGoaster | 128/419 R |
| 4,173,229 | 11/1979 | Halfon | 128/419 R |
| 4,323,073 | 4/1982 | Ferris | 128/419 R |
| 4,406,658 | 9/1983 | Lattin et al. | 128/419 R |

FOREIGN PATENT DOCUMENTS 2516022  2/1976  Fed. Rep. of Germany ...... 128/391

Primary Examiner—William E. Kamm
Assistant Examiner—Mitchell J. Shein
Attorney, Agent, or Firm—Hill, Van Santen, Steadman & Simpson

[57] ABSTRACT

Disclosed herein is an instrument for the electrotherapeutic self-treatment of pain and insomnia comprising a set of three plates, coplanar one with respect to the other and interspaced, the two outside ones of which are connected to the negative pole of a current generator constituted by a microbattery, while the one in the center is connected to the positive pole. The outside plates and the one in the center define electrodes made of metal of different characteristics, the former zinc and the latter brass.

In this way, two different electric fields are originated: one at the surface due to the diversity in the nature of the electrodes and one deep-seated due to the auxiliary generator.

7 Claims, 5 Drawing Figures

FIELD PRODUCING INSTRUMENT FOR THE ELECTROTHERAPEUTIC SELF-TREATMENT OF PAIN AND INSOMNIA

BACKGROUND OF THE INVENTION

The invention relates to a personal use field producing instrument of a new type for the electrotherapeutic self-treatment of pain and insomnia, constituted by a very small device whose dimensions and lightness are such as to render it suitable to be applied directly, held in position by means of a plaster or anything else able to maintain it in close contact, to any painful part of the body for an unlimited amount of time both during the day and the night. The solution evolved is, in fact, the fruit of ambition whereby it be possible for all and sundry to possess a personal instrument that fits into the pocket and has the ability to eliminate pains, free one from anxiety and depression, overcome insomnia, cure colds and provide a remedy for the annoyance of snoring, without encumbering leads or other application dependent items.

Though falling within the category of electric transcutaneous nerve stimulators, the instrument according to the invention is in no way based on the same principle as other instruments constructed to date, nor does it have any of the problems that can be seen to arise therewith.

DESCRIPTION OF THE PRIOR ART

Transcutaneous electrostimulators currently marketed are, in fact, generally constituted by oscillators or impulse generators that stimulate the nerves by means of plates rested on the skin, are connected by wires to the generator and with which the following main problems arise:

1. it is not always easy for the uninitiated to adjust the frequency, voltage and current intensity appropriately;
2. side effects that irritate the skin, though attributable to misuse of the instrument;
3. set, precise and limited periods of application for each treatment;
4. tediousness of the treatment;
5. high cost.

Furthermore, the dimensions and the weight of the said electrostimulators prevent them from being put in the pocket, while the leads running from the plates to the generator do not permit unobserved use in the daytime when others are present.

In addition to what has been stated above, the said plates cannot be applied properly onto the acupuncture meridian points, they do not combat anxiety, depression, insomnia and snoring, and they cannot be applied to the skin for an unlimited period of time.

SUMMARY OF THE INVENTION

The object of the invention is not to produce side effects and for it to be able to be used in acupressure or "Schiatzu" applications, facilitating, with the expressly studied plates thereof, the locating on the part of the person using the instrument on him or herself, the classic points in acupuncture, and ridding him or her of the difficulty of regulating the duration and the more or less heavy pressure of the fingers or of the massage prescribed for common acupressure applications.

The instrument in question can be applied to painful parts of the body in order to cause the pain to disappear, digestion to be encouraged or to eliminate abdominal swelling, as well as to combat constipation; it can be rested on any part of the musculature or nervous tissues to remove discomfort and weariness; it can be held in the hand during the day and be applied to the inside or the outside of the ankle, or to the wrist in bracelet form to give back vigour and energy to the whole body, foster contact between the body and the mind and, therefore, produce profound relaxation; to overcome syndromes of tension, states of anxiety, shoulder ache, back ache, migraine and slight hypertension; to revitalize debilitated hypotonic muscles rendered weak through illness or some other reason; it can be applied to topical parts in order to arouse and enhance virility etcetera.

The instrument according to the invention is, therefore, totally different from any other existing electrostimulator because of the highly original principle on which it is based, because of the greatly reduced dimensions thereof, because of the extreme lightness thereof, because of the application simplicity thereof, because of the modest cost whereby the purchase thereof is possible for everyone and, above all, because of the wider range of therapeutic applications. Even when utilizing pulsating current it creates, at dermal level depth, two very weak double electromagnetic fields, each of which generated by an electric field.

The absolute novelty on which the instrument in question is based consists, in fact, in the production of two very weak double electric fields: one superficial at cornifiable level and the other at dermal level depth, each of which creates an electromagnetic field. In this way, there is a union of the effects of galvanism and electromagnetism with the exceptional and stupefying results that a vast amount of data has shown there to be.

BRIEF DESCRIPTION OF THE DRAWINGS

The instrument forming the subject of the invention is illustrated on the accompanying drawings, in which.

DESCRIPTION OF THE PREFERRED EMBODIMENTS

Figure 1:
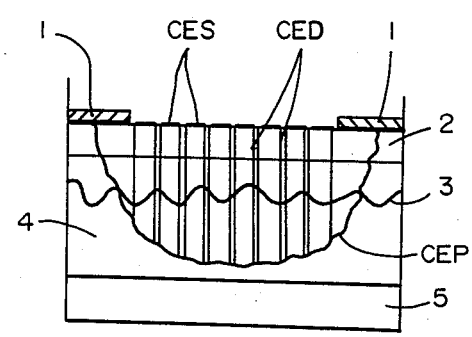
FIG. 1 shows an example of the electric fields generated by the instrument in question on a dermal area illustrated in sectional form.

The aforementioned principle is illustrated in FIG. 1 of the accompanying table with a point of application of a pair of electrodes 1 on an area where at 2 is indicated the stratum corneum of the skin; at 3 the stratum germinativum; at 4 the dermis; and at 5 the hypodermis.

The bars or horizontal plates numbered 1 represent, as stated, the electrodes rested on the skin, while the horizontal dashes there in between, indicated with the letters CES, represent the molecules of the electrically activated diaphoretic solution.

The sinusoidal section terminating at the electrodes, indicated with the letters CEP, shows the hypothetical direction of each artificial electric field generated by the said electrodes, while the vertical black sections between the superficial electric field CES and the artificial electric field CEP at dermal level depth show the lines of the double electromagnetic field CED that is produced between the two electric fields.

Substantially, the superficial electric fields CES are obtained by the electrization of the diaphoretic solution, while the deep-seated artificial electric fields CEP are produced by a battery operated current generator that operates in between the two plates 1.

Figure 3:
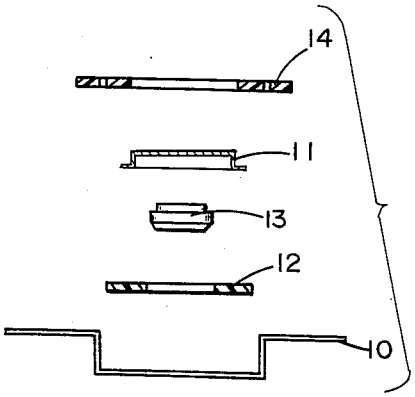
FIG. 3 shows, in a lateral view, the elements depicted in FIG. 2.
Figure 2:
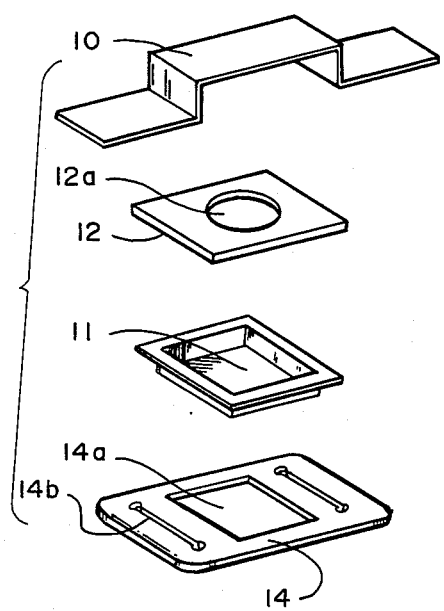
FIG. 2 shows, in an exploded view, the elements constituting the instrument in question in a first embodiment thereof.
Figure 4:
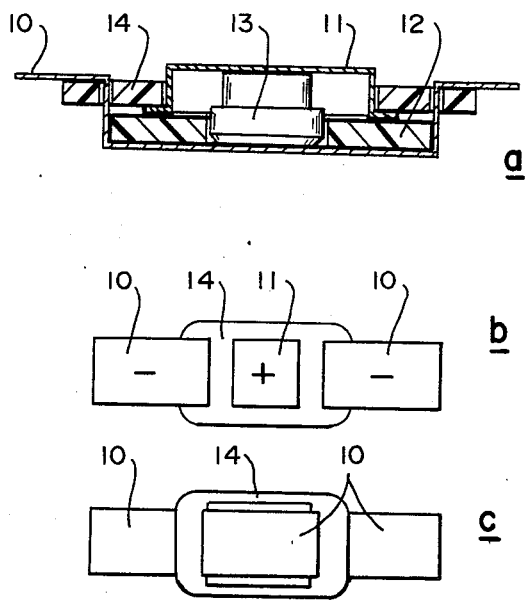
FIG. 4 shows the instrument according to FIGS. 2 and 3 in the assembly configuration and in a view from above, from below and in sectional form.

The foregoing form of realization is shown in a first embodiment illustrated in FIGS. 2, 3 and 4.

Indicated in the said figures at 10 are a pair of negative electrodes obtained from the terminal parts of the bending of a metal bar (that can be made of iron, zinc, nickel or some other common metal), while at 11 is shown the positive electrode (made of gold, brass or some other precious metal).

In the center of the negative electrodes 10 fashioned out of the bar (that can be plastified or in some way have the upper part thereof insulated) is placed a gasket of rubber or some other insulating material, shown at 12, destined to house in the central part 12a thereof, a microbattery 13, the negative pole of which is placed in contact with the central bend in the metal bar 10 (see also FIG. 4). The positive pole of the microbattery is, instead, inserted and placed in contact with the positive electrode 11 and this, in turn, is inserted in the aperture 14a in the center of a support 14 made of polyethylene or another plastic material or, at any rate, one that insulates.

The instrument is then assembled by inserting the two negative electrodes of the bar 10 into the lateral slits 14b provided in the support 14 (see FIG. 2) in such a way as to achieve the result illustrated in FIG. 4.

In particular it is possible, in the last mentioned figure, to see: (a) a longitudinal sectional view of the instrument; (b) a view from below, that is to say, the utilization side of the instrument; (c) a view from above In this simple embodiment it is, therefore, possible to observe that the instrument illustrated in, for example, FIG. 4b, has the two electrodes 10 and 11 separated one from the other by the insulating support 14 in such a way that two double electric fields are generated between the two extremity terminals of the negative electrode 10 and the central terminal of the positive electrode 11.

More precisely, between the positive electrode and each negative electrode (as can be seen in FIG. 1), when these are rested on the skin, a superficial circulation of direct current is originated in a very short space of time due to an electrochemical process resulting from the different chemical nature of the said electrodes which, as stated, are made of metal whose characteristics are dissimilar and are suited to the purpose.

This superficial electric current CES determines the electrolytic dissociation of the saline solution contained in and constituted by the sweat, and thus the ions migrate and deposit their charges onto the electrodes (from the positive one to the negative one and vice versa) giving rise to two circulations of current at surface level.

Contemporaneously, again as illustrated in FIG. 1, the direct current generated and circulating between the electrodes, due to the microbattery 13, creates an artificial electric field CEP at dermal depth and this, with the preceding superficial electric field CES, produces a double electromagnetic field indicated with the letters CED.

In this way, there is a multiplication (also on account of the presence of the two negative electrodes) of the hyperaemic effects of the galvanism and, therefore, reassorption of the products of eventual inflammatory processes determined by the improved circulation of blood in the organism, as well as nervous stimulation, highly important for solving a series of acute and chronic inflammatory states, such as contusions, sprains, fibrositis, arthritis, neuritis and neuralgia; the foregoing in addition to the thermal and analgesic effects, as well as the consistent mechanical effect, that exert a direction action on the nerves, in a sort of micromassage produced by the double electromagnetic fields.

The instrument in question, therefore, essentially makes use, on one hand, of the properties of each element or metallic compound that are called the "normal potential of the electrodes" which when different in nature and placed in contact with a saline solution, generate a flow of current and, in particular, a flow of ionic charges; on the other hand, the said instrument utilizes in the most rational and functional way, the depth field generated by the difference in artificial potential existing between the said electrodes.

Figure 5:
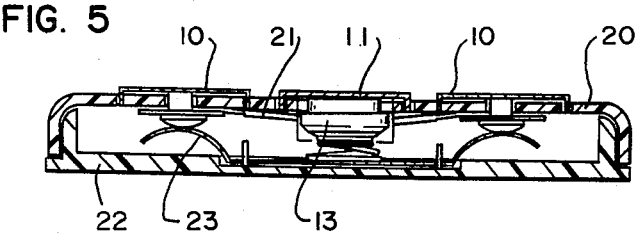
FIG. 5 shows, in a longitudinal sectional view, the instrument in question in a second embodiment.

In conclusion, illustrated in FIG. 5 is another example of an embodiment for the instrument in question wherein the said instrument is constituted substantially by an external containment casing composed of an underneath plastic material part 22 and an upper covering part 20, the latter also made of plastic material.

Protruding from the top of the said casing are three plates that constitute the electrodes of the instrument, and more precisely there are two outside plates 10 riveted to the cover 20, and a plate 11 in the center that constitues the positive electrode.

The outside plates 10 are interconnected electrically by means of a wire 21 and the underneath part thereof is placed in contact with a spring 23 connected electrically to the negative pole of the microbattery 13, the positive pole of this being placed in direct contact with the plate 11 that constitutes the positive electrode. In particular, it is envisaged that the said central plate be removably slotted into the cover 20 in such a way that the substitution be possible of the microbattery 13 when discharged.

Numerous modifications of a practical nature may be made to the instrument according to the invention without, because of this, in any way deviating from the framework of protection afforded thereto, as described herein and claimed hereunder.

What is claimed is:

1. Field producing instrument for the electrotherapeutic self-treatment of pain and insomnia, comprising: a supporting body having a sealing element made of insulating material, and providing a compact instrument configuration, a first pair of metal electrodes supported by said sealing element at opposite extremities thereof, a second metal electrode, insulated from the said first pair of metal electrodes, and disposed centrally of said sealing element and between said first pair of metal electrodes, wherein the said second electrode is made of a metal different from that of the said first pair of metal electrodes; and a microbattery having a first pole electrically connected with said first pair of metal electrodes and having a second pole electrically connected with said second metal electrode; said supporting body having a receptacle therein for the housing of said microbattery.

2. Instrument according to claim 1, wherein the first pair, and second metal electrodes are constituted by a set of metal plates, that are coplanar and slightly apart from one another.

3. Instrument according to claim 1, wherein the potential of said first pair of metal electrodes is lower than that of said second metal electrode, the first pole of the microbattery being a negative pole and the second pole of the microbattery being a positive pole.

4. Instrument according to claim 1, wherein at least said second metal electrode is removable in such a way that the microbattery can be replaced.

5. Instrument according to claim 1 wherein the first pair of metal electrodes are formed by the extremities of a centrally U-bent metal plate, which centrally defines a portion of the receptacle for the housing of said microbattery.

6. Field producing instrument for the electrotherapeutic self-treatment of pain and insomnia, comprising a low potential source of current, electrodes made of metallic materials that differ one from the other, connected electrically to the low potential source of current, said source of current having a positive pole and a negative pole, and said electrodes comprising a central electrode connected electrically to the positive pole of the source of current, and a pair of outside electrodes, placed bilaterally to the central electrode, and connected electrically to the negative pole of said source, wherein said source is constituted by a microbattery having said positive pole and said negative pole and the instrument itself provides a receptacle containing said microbattery and comprises an underneath supporting body and an upper sealing element, both made of insulating material and designed to cooperate in securing the central electrode and the outside electrodes and the microbattery as a unit therewith, the upper sealing element being provided at the extremities thereof with a pair of zinc plates that constitute the outside electrodes, and being provided in the center with receiving means for the reception of a brass central plate that constitutes the central electrode and, underneath, is placed in contact with the positive pole of the said microbattery.

7. A method for the electrotherapeutic self-treatment of pain and insomnia comprising applying at the point of the body to be treated, a combination of superficial electric fields with deep-seated electric fields and generating the superficial electric fields by causing the migration of superficial ionic charges in the diaphoretic solution of the patient, between a pair of outer metal electrodes and a central metal electrode in the center therebetween, wherein said central electrode is made of metal different from that of said pair of outer metal electrodes, and producing the deep-seated electric fields with a microbattery electrically connected to said pair of outer metal electrodes and said central metal electrode.

* * * * *